United States Patent
Wainer et al.

(10) Patent No.: US 6,794,653 B2
(45) Date of Patent: Sep. 21, 2004

(54) SPECT FOR BREAST CANCER DETECTION

(75) Inventors: Naor Wainer, Zichron Yaakov (IL);
Yaron Hefetz, Herzelia (IL)

(73) Assignee: Elgems Ltd., Tirat Hacarmel (IL)

( * ) Notice: Subject to any disclaimer, the term of this patent is extended or adjusted under 35 U.S.C. 154(b) by 0 days.

(21) Appl. No.: 10/426,543

(22) Filed: Apr. 30, 2003

(65) Prior Publication Data

US 2003/0197127 A1 Oct. 23, 2003

Related U.S. Application Data

(63) Continuation of application No. 09/587,580, filed on Jun. 5, 2000, now Pat. No. 6,696,686.

(30) Foreign Application Priority Data

Jun. 6, 1999 (IL) .................................. PCT/IL99/00301

(51) Int. Cl.[7] .............................. G21K 1/02; G01T 1/24; H01J 1/52
(52) U.S. Cl. .............................. 250/363.01; 250/370.09
(58) Field of Search ......................... 250/363.01, 505.1, 250/370.09, 363.05

(56) References Cited

U.S. PATENT DOCUMENTS

| | | |
|---|---|---|
| 5,451,789 A | 9/1995 | Wong et al. |
| 5,519,221 A | 5/1996 | Weinberg |
| 5,534,701 A | 7/1996 | Pierfitte et al. |
| 5,587,585 A | 12/1996 | Eisen et al. |
| 5,774,802 A | 6/1998 | Tell et al. |
| 6,242,743 B1 | 6/2001 | DeVito et al. |
| 6,271,524 B1 | 8/2001 | Wainer et al. |
| 2002/0143249 A1 * | 10/2002 | Tornai et al. ............... 600/425 |

FOREIGN PATENT DOCUMENTS

| | | |
|---|---|---|
| JP | 58-223081 | 12/1983 |
| JP | 61-159179 | 7/1986 |
| JP | 62-52479 | 3/1987 |
| WO | WO 98/23974 | 6/1998 |

* cited by examiner

*Primary Examiner*—Georgia Epps
*Assistant Examiner*—Alicia M Harrington
(74) *Attorney, Agent, or Firm*—Feaster & Company

(57) ABSTRACT

A nuclear imaging system for imaging of the breast including at least one gamma camera, having a radiation detecting surface, which detects gamma radiation and provides data signals responsive to radiation from the breast and a collimator, positioned over the reception surface. The system includes a gantry on which the radiation detector is mounted and which provides rotational movement of the radiation detection surface around the axis of the breast and a computer which receives and analyzes the data signals and constructs an image of radiation sources therefrom. The radiation detection surface of the at least one gamma camera is tilted with respect to the axis during rotation of the at least one gamma camera about the axis, such that it is partially facing the chest of a study subject. Alternatively, the collimator has septa its center which accept radiation from a direction perpendicular to the radiation detection surface and septa near an edge of the collimator which accept radiation from an outward facing acute angle to the perpendicular direction.

37 Claims, 7 Drawing Sheets

SPECT FOR BREAST CANCER DETECTION

RELATED APPLICATION

This application is a continuation of U.S. application Ser. No. 09/587,580, filed on Jun. 5, 2000 now U.S. Pat. No. 6,696,686.

FIELD OF THE INVENTION

The present invention relates generally to SPECT instruments and in particular to a small SPECT device, dedicated to breast imaging.

BACKGROUND OF THE INVENTION

SPECT is one of several nuclear imaging techniques. Generally, in nuclear imaging, a radioactive isotope is injected to, inhaled by or ingested by a patient. The isotope, provided as a radioactive-labeled pharmaceutical (radio-pharmaceutical) is chosen based on bio-kinetic properties that cause preferential uptake by different tissues. The gamma photons emitted by the radio-pharmaceutical are detected by radiation detectors outside the body, giving its spatial and uptake distribution within the body, with little trauma to the patient.

FIG. 1 illustrates a general nuclear-imaging detector 10 comprising a NaI(T1) scintillation crystal 12. Generally, scintillation crystal 12, of a diameter $D_1$, is large enough to image a significant part of the human body (typically 40 cm). An array of photo-multiplier tubes (PMTs) 14 view scintillation crystal 12, to give positional sensitivity. Each PMT 14 has an x and a y coordinate. When a photon is absorbed by scintillation crystal 12, light is generated. A number of PMTs 14 receive the light and produce signals. The X and Y coordinates of the event are determined by the strength of the signals generated by each PMT. The energy of the event is proportional to the sum of the signals, called the Z signal. Only Z signals within a given range are counted.

Semiconductors with high atomic numbers and relatively high densities such as CdZnTe, CdTe, $HgI_2$, InSb, Ge, GaAs, Si, PbCs, PbCs, PbS, or GaAlAs, have a high stopping power and can be used as gamma ray detectors with good photon detection efficiencies, good spatial resolution, and a relatively high photon-energy resolution. Solid state semiconductor gamma cameras generally comprise arrays of pixelated detector, hereinafter referred to as "pixelated detectors". One type of pixelated detector is described in PCT publication WO 98/23974, the disclosure of which is incorporated herein by reference. FIG. 2 shows a typical construction of a pixelated detector 20 comprising a crystal 22 formed from a semiconductor material such as one of those noted above. A face 24 of crystal 22 has a large single cathode electrode 26. An opposite face 28 of crystal 22 has an anode 30 comprising a rectangular array of identical small square anode pixels 32. Typically, sizes of anode pixels 32 vary between 1 and 4 $mm^2$, and the thickness of crystal 22, between anode 30 and cathode 26 is on the order of millimeters to a centimeter. In operation, a voltage difference is applied between anode and cathode so that an electric field, hereinafter referred to as a "detector field", is generated in crystal 22. This field is typically on the order of a few kilovolts per centimeter.

When a photon, having an energy typical of the energies of photons used in gamma cameras, is incident on crystal 22, it generally loses all its energy in crystal 22 by ionization and produces pairs of mobile electrons and holes in a localized region of crystal 22. As a result of the detector field, the holes drift to cathode 26 and the electrons drift to anode 30, thereby inducing charges on anode pixels 32 and cathode 26. The induced charges on anode pixels 32 are sensed and generally partially processed by appropriate electronic circuits located in a detector base 34 to which detector 20 is mounted. Signals from the induced charges on pixels 32 are used to determine the time at which a photon is detected, how much energy the detected photon deposited in the crystal and where in the crystal the photon interaction took place.

Generally, a collimator 16 is placed between scintillation crystal 12 or 22 and the tissue. Commonly, collimator 16 is honeycomb shaped, comprising a large number of holes separated by parallel lead septa. The purpose of collimator 16 is to intercept and eliminate gamma-ray photons that are not traveling in an accepted direction, parallel to the lead septa. The geometric configuration of collimator 16 (e.g., the size and shape of the holes and the length of lead walls) determine the geometric response function of collimator 16. In general, there is a tradeoff in which the collection efficiency of detector 16 increases as the geometric response function widens and the spatial resolution decreases.

SPECT (Single-Photon-Emission Computed Tomography) is based on conventional nuclear imaging technique and tomographic reconstruction methods, wherein projection (or planar) data acquired from different views around the patient are reconstructed, using image reconstruction methods, to generate cross-sectional images of the internally distributed radio-pharmaceuticals. SPECT images provide enhanced contrast, when compared with planer images obtained with conventional nuclear imaging methods.

A typical SPECT system consists of a single or multiple units of radiation detectors arranged in a specific geometric configuration, a mechanism for moving the radiation detectors and/or a specially designed collimator to acquire data from different projection views.

A typical system is based on a single or multiple scintillation cameras, mounted on a rotating gantry. This may consist of a single-camera system, a dual-camera system, a triple-camera system or a quadruple-camera system. Generally, camera-based SPECT systems use Anger scintillation cameras such as those used in conventional planar nuclear medicine. These cameras allow for truly three-dimensional imaging, by providing a large set of contiguous trans-axial images that cover the entire organ of interest. They are easily adaptable for SPECT imaging of the brain or body, by simply changing the radius of rotation of the camera. Because of the relatively low counting rate capability, it is desirous to use two or more cameras. The increase in sensitivity per slice is proportional to the number of cameras.

The most common collimator systems for SPECT systems are parallel-hole collimators, wherein the septa are perpendicular to the scintillation crystal. As noted above, there is an unavoidable tradeoff between detection efficiency and spatial resolution of parallel-hole collimators. An alternative design is a converging-hole collimator that increases the angle of acceptance of incoming photons. Examples of these special collimator designs and their points of convergence are given in FIGS. 3A–3D. FIG. 3A illustrates a parallel-hole collimator. FIG. 3B illustrates a fan-beam collimator, where the collimator holes are converged to a line that is parallel to the axis of rotation. FIG. 3C illustrates a cone-beam collimator, where the collimator holes are converged to a point. FIG. 3D illustrates a varifocal collimator, where the collimator holes are converged to various focal points. Converged collimators have smaller fields of view when compared with parallel-hole collimators.

In general, camera-based SPECT systems may be comprised of detectors that rotate about the region to be imaged or arrays of detectors that completely surround the region to be imaged, for example with a ring of detectors. In either event, the object of the imaging system is to acquire data from directions including at least 180 degrees of view.

SPECT breast imaging is especially challenging, since there is no way to acquire cross-sectional data suitable for analytic tomographic reconstruction, especially from slices near the chest wall, from the front of the patient, since there is no way to acquire views of a slice over 180 degrees of view. Furthermore, rotating around the axis of the patient is not desirable due to the distance of the back of the body from the breast and the amount of radiation from the body which may overwhelm the radiation emitted from the breast.

SUMMARY OF THE INVENTION

An aspect of some embodiments of the present invention relates to providing a small SPECT system, dedicated to the nuclear imaging of the breast. In exemplary embodiments, the SPECT system is positioned on a gantry, so as to be substantially parallel with the axis of the breast and perpendicular to the body. The axis of the breast is a vertical line passing through the nipple when the test subject is lying face downward and prone, with the breast passing through a hole in the surface supporting the patient or a similar line. In an embodiment of the invention, the SPECT system rotates substantially around the axis of the breast. The patient may lay prone on a table, facing down, with the breast protruding through a hole in the table and thus pulled down by gravity. Additionally or alternatively, the breast may be pulled out by a vacuum pump. Alternatively, other means for extending the breast may be used.

In some embodiments that incorporate this aspect, the SPECT system comprises a single scintillation camera that rotates about the breast. Alternatively, the SPECT system comprises a plurality of scintillation cameras, arranged around the axis of rotation, in order to enhance the system sensitivity. In other embodiments of the invention, a plurality of ring-shaped detectors arranged about the breast may be used. In still other embodiments of the invention, a plurality of detector bars, arranged about the axis of the breast to form a ring of detectors, may be used.

In some embodiments that incorporate this aspect, the total scintillation-crystal length is longer than the breast and covers the length of the breast in one rotational pass. Alternatively, several rotational passes are required, at different breast "heights" to cover the length of the breast.

In some embodiments that incorporate this aspect, the face of the camera or detectors are parallel to the axis of the breast. Alternatively, the camera is mounted on a pivot or a hinge and can be tilted at various angles with respect to the axis of the breast. In some embodiments, one or more rotational passes are made with the detectors at a acute angle with the axis of the breast, for imaging of the breast near the chest wall, and another rotational pass is made with the detectors parallel with the axis of the breast, for imaging of the main portion of the breast.

In some embodiments that incorporate this aspect, the camera-based SPECT system comprises at least one NaI(T1) crystal and an array of PMTs for determining position. Alternatively, a single position sensitive PMT views the crystal. Alternatively, the camera-based SPECT system comprises at least one pixelated solid-state detector, which is smaller and more suitable for use as a small camera. Due to the constricted space between the breast and the importance of imaging the region near the chest wall, small cameras are especially useful in carrying out the invention.

An aspect of some embodiments of the present invention relates to providing a small multidetector SPECT system, dedicated to the nuclear imaging of the breast. In an embodiment of the invention, an arrangement of four cameras, arranged in a square around the breast, is used. The cameras may be rotated around the breast. Alternatively, a stationary circular ring of detectors is used.

An aspect of some embodiments of the present invention relates to providing a special collimator for improved imaging of the chest wall. Preferably, the collimator comprises septa having a diverging field of view on the edge of the collimator adjacent to the chest wall (diverging-hole collimator). In an embodiment of the invention, the direction of the septa changes away from the chest wall edge to provide a view parallel to the rotation axis (approximately equal to the axis of the breast). In this embodiment, reconstruction may be done by an iterative method at least for slices at least near the chest wall. For portions of the breast away from the chest wall, either iterative or analytic (back-projection) methods may be used.

There is thus provided, in accordance with an embodiment of the invention, a system for the nuclear imaging of the breast, comprising:

at least one gamma camera, of a size appropriate for the scanning of a breast, having a radiation detecting surface, which detects gamma radiation and provides data signals responsive to radiation from the breast;

a collimator, positioned over the reception surface;

a gantry on which the radiation detector is mounted and which provides rotational movement of the radiation detection surface around the axis of the breast; and a computer which receives and analyzes the data signals and constructs an image of radiation sources therefrom.

Optionally, the at least one gamma camera comprises a plurality of gamma cameras placed about and facing the axis of rotation. Optionally, the plurality of gamma cameras are symmetrically placed around the axis of rotation.

In an embodiment of the invention, the radiation detection surface of the at least one gamma camera is tilted with respect to the axis during rotation of the at least one gamma camera about the axis, such that it is partially facing the chest of a study subject.

There is further provided, in accordance with an embodiment of the invention a system, for the nuclear imaging of the breast, comprising:

at least one gamma camera, of a size appropriate for the scanning of a breast, having a radiation detecting surface, which detects gamma radiation and provides data signals responsive to radiation from the breast;

a collimator, positioned over the reception surface;

a gantry on which the radiation detector is mounted and which provides rotational movement of the radiation detection surface around the axis of the breast; and a computer which receives and analyzes the data signals and constructs an image of radiation sources therefrom, wherein the radiation detection surface of the at least one gamma camera is tilted with respect to the axis during rotation of the at least one gamma camera about the axis, such that it is partially facing the chest of a study subject.

Optionally, the system includes means for selectively tilting the at least one gamma camera such that the radiation detection surface is selectively tilted or parallel to the axis of rotation, during rotation of the at least one gamma camera about the axis.

Optionally, the collimator comprises septa near the center of the collimator which accept radiation from a direction perpendicular to the radiation detection surface and septa near an edge of the collimator which accept radiation from an outward facing acute angle to the perpendicular direction.

There is further provided, in accordance with an embodiment of the invention a system, for the nuclear imaging of the breast, comprising:

at least one gamma camera, of a size appropriate for the scanning of a breast, having a radiation detecting surface, which detects gamma radiation and provides data signals responsive to radiation from the breast;

a collimator, positioned over the reception surface;

a gantry on which the radiation detector is mounted and which provides rotational movement of the radiation detection surface around the axis of the breast; and a computer which receives and analyzes the data signals and constructs an image of radiation sources therefrom, wherein the collimator comprises septa near the center of the collimator which accept radiation from a direction perpendicular to the radiation detection surface and septa near an edge of the collimator which accept radiation from an outward facing acute angle to the perpendicular direction.

Optionally, the septa which accept radiation near one edge accept such radiation only near one edge of the collimator. Optionally, the one edge is an edge near the chest wall of the study subject.

In an embodiment of the invention, the computer constructs the image of radiation sources utilizing an iterative approach for at least part of a reconstructed volume.

In an embodiment of the invention, the computer constructs the image of the radiation source utilizing an iterative approach for at least a portion of the volume for which data is acquired with the radiation detection surface at the angle. An analytic approach is used for at least a part of the volume for which data is acquired with the radiation detection surface parallel to the angle or rotation.

In an embodiment of the invention, the detector is a detector having an extent between 10 and 20 cm. More preferably, the extent is between 10 and 15 cm. A suitable extent is about 12 cm.

There is further provided, in accordance with an embodiment of the invention, a gamma ray detector system comprising:

at least one gamma ray detector having a detector surface that has a normal thereto at each point thereof; and at least one collimator placed on the detector surface, the collimator having a first portion that selectively passes gamma rays which impinge it at the normal angle and at angles near said angle and a second portion that selectively passes gamma rays which impinge on it from an outward looking direction with respect to the normal;

wherein the first portion comprises a region near one edge of the collimator and a central region of the collimator and wherein the second portion comprises a region near a second edge of the collimator opposite the one edge.

Optionally, the at least one detector surface is a planar surface and wherein the first portion comprises the entire planar surface except for a region near the second edge.

In an embodiment of the invention, the detector is a detector having an extent of less than 20 cm. Optionally, the extent is less than 15 cm.

In an embodiment of the invention, the at least one detector comprises first and second detectors the first detector and second detectors having first and second detector surfaces that are parallel and face each other, each said detector having a collimator placed thereon, as aforesaid. Optionally, the second portions of the collimators associated with the first and second detectors are situated opposite each other.

In an embodiment of the invention, the detector surface comprises a cylindrical surface and wherein the first portion comprises the detector surface except for a region near one end of the cylindrical surface. The cylindrical surface may have an inner diameter of between 10 and 20 cm. The collimator has an inner diameter of less than 20 cm. Optionally, the collimator has an inner diameter of less than about 15 cm.

There is further provided, in accordance with an embodiment of the invention, a gamma camera comprising a gamma ray detector system according to the invention and including a rotator that rotates the at least one detector surface about an axis parallel to and within the field of view of the detector surface, wherein the outward looking direction is at an acute angle with the axis. Optionally, the outward looking angle varies over the second portion, with the angle being 90 degrees near the first portion and a minimum value near at the second edge. Optionally, the minimum value is about 60 degrees.

In an embodiment of the invention, the gamma ray detector system is sized and configured to rotate about a breast of a human patient, wherein the axis of rotation coincides generally with the axis of the breast.

In an embodiment of the invention, the at least one detector generates nuclear medicine imaging signals responsive to gamma rays detected by the at least one detector and including image processing circuitry that receives the signals and produces a three dimensional image therefrom. Optionally, the image processing circuitry produces the image utilizing an iterative approach for a portion of the image, the portion including at least the portion including information acquired from the outward looking direction.

In an embodiment of the invention, the outward looking angle varies over the second portion, with the angle being 90 degrees near the first portion and having a minimum value near at the second edge. Optionally, the minimum value is about 60 degrees.

In an embodiment of the invention, the gamma ray detector system is sized and configured to fit around the breast of a human patient, wherein the axis of the cylinder coincides generally with the axis of the breast.

In an embodiment of the invention, the cylindrical detector generates nuclear medicine imaging signals responsive to gamma rays detected by the detector and including image processing circuitry that receives the signals and produces a three dimensional image therefrom.

Optionally, the image processing circuitry produces the image utilizing an iterative approach of a portion thereof, the portion including at least the portion from which imaging information is acquired from the outward looking direction.

There is further provided, in accordance with an embodiment of the invention, a method of imaging of the breast using gamma rays, comprising:

acquiring gamma ray data from the breast of a subject utilizing a gamma ray detector head generally parallel to the axis of the breast; and reconstructing a three dimensional image of a radiopharmaceutical in the breast.

Optionally, acquiring gamma ray data comprises acquiring date from gamma rays emanating from tissue near the chest wall of the subject. In a preferred embodiment of the invention, the chest wall data is incomplete in the sense that it does not allow for analytic reconstruction of the distribution.

Optionally, reconstructing a three dimensional distribution comprises utilizing an iterative algorithm at least for regions of the breast for which an analytic solution is not possible.

Optionally, an iterative algorithm is used for reconstructing the distribution in portions of the breast and an analytic algorithm is used for reconstruction of the distribution of portions of the breast.

There is further provided, in accordance with an embodiment of the invention, 43. A method of imaging using gamma rays, comprising:

acquiring gamma ray data from a subject utilizing at least one gamma ray detector head; and reconstructing a three dimensional image of the sources of the gamma rays, utilizing an iterative approach for a first portion of the volume for which data is acquired and utilizing an analytic approach for a second portion of the volume for which data is acquired.

In an exemplary embodiment the first portion includes a volume for which said gamma ray data does not include a full set of tomographic data.

BRIEF DESCRIPTION OF THE DRAWINGS

Exemplary embodiments of the invention are described in the following detailed description of the preferred embodiments of the invention together with the attached drawings, in which same number designations are maintained throughout the figures for each element and in which.

DETAILED DESCRIPTION OF EMBODIMENTS

Figure 1:
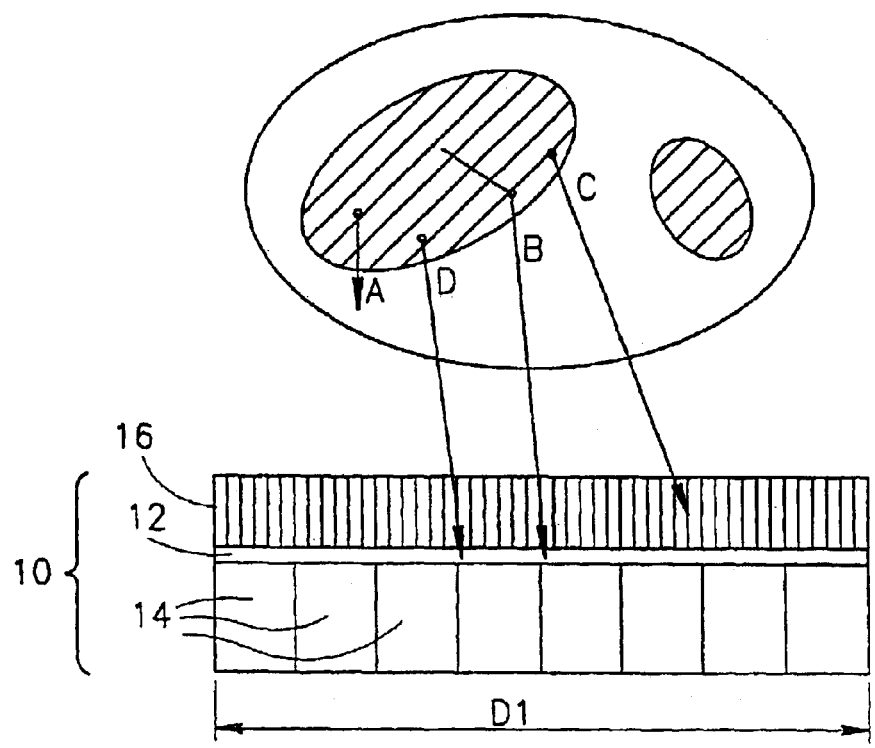
FIG. 1 is a schematic illustration of a nuclear-imaging detector, comprising an NaI(T1) scintillation crystal, as known in the art.
Figure 2:
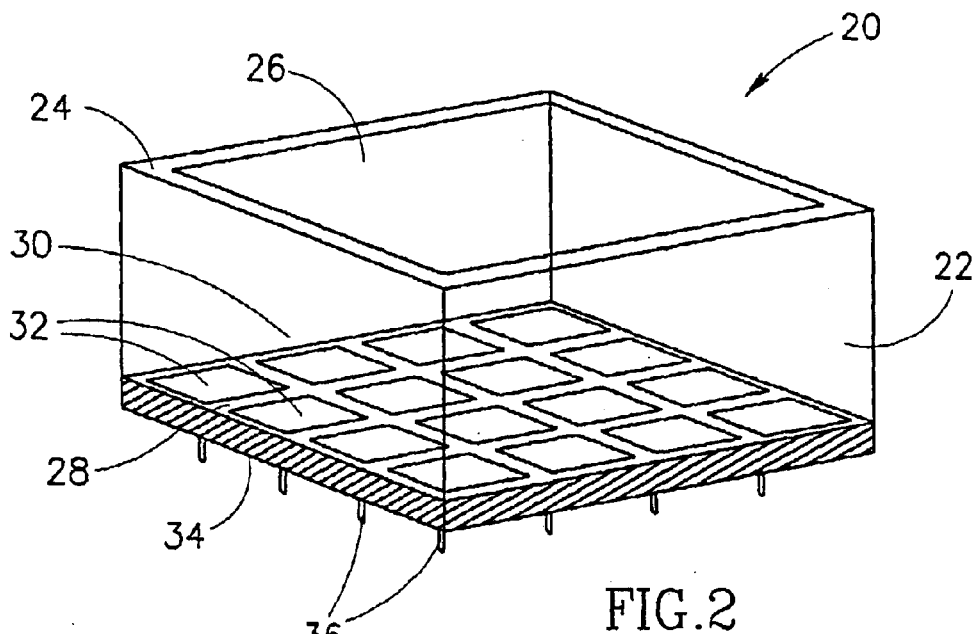
FIG. 2 is a schematic illustration of a pixelated, solid-state scintillation detector, as known in the art.
Figure 3A:
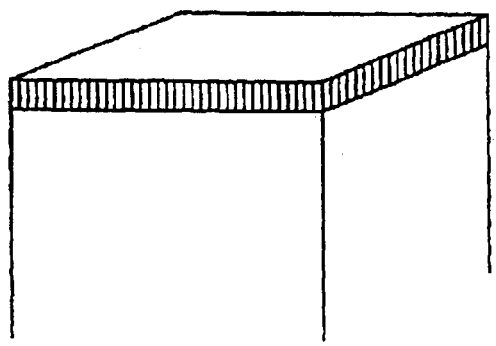
FIGS. 3A–3D are schematic illustrations of special collimator designs, as known in the art.
Figure 3B:
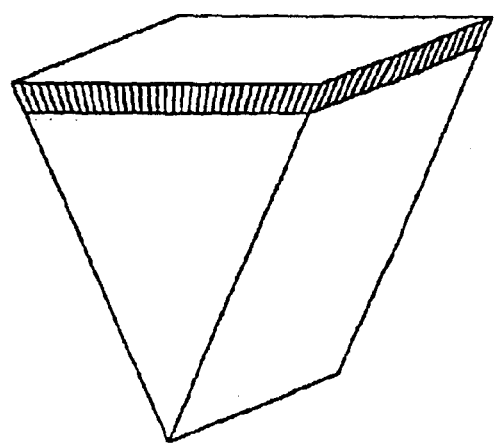
Figure 3C:
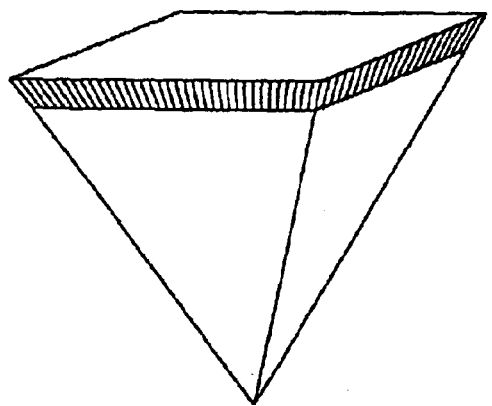
Figure 3D:
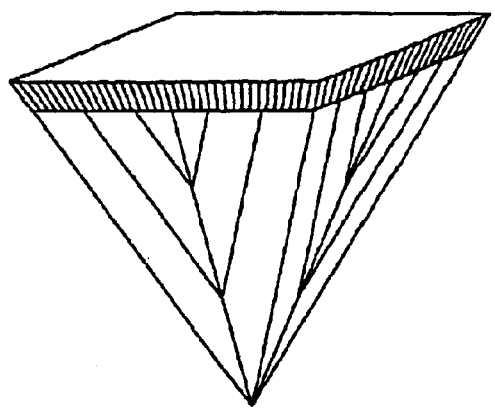
Figure 4:
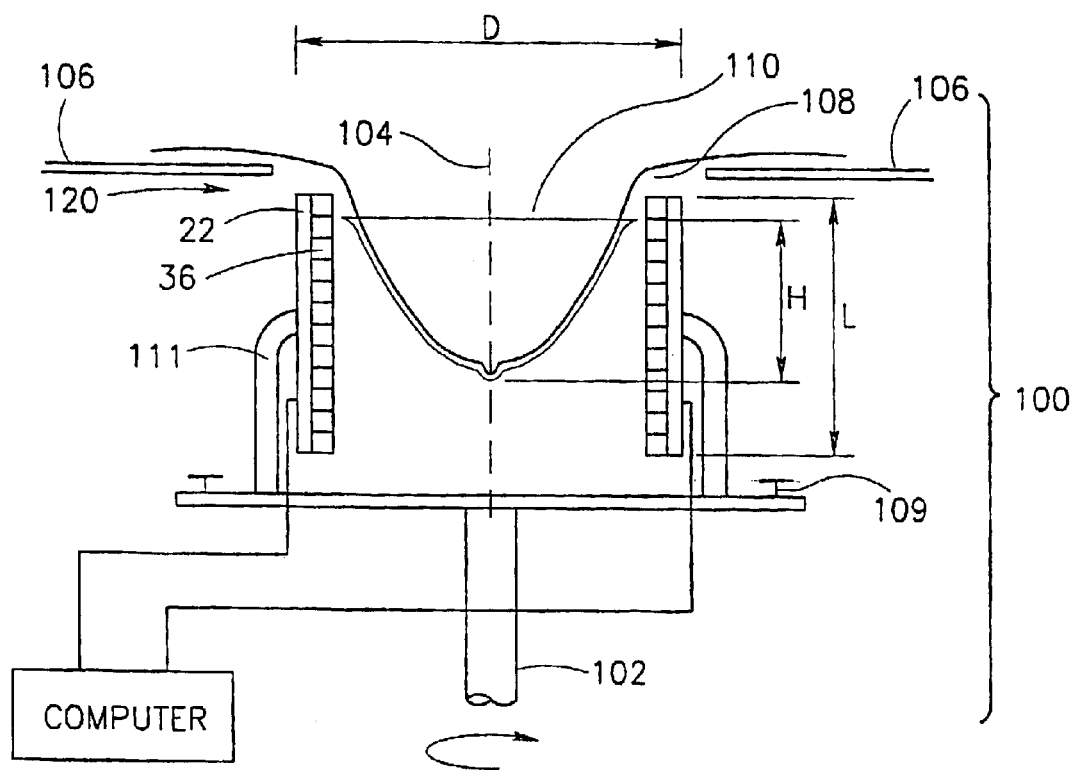
FIG. 4 is a schematic illustration of a small, camera-based SPECT system dedicated to the nuclear imaging of the breast, wherein the camera is rotated about an axis parallel with the axis of the breast, in accordance with an embodiment of the present invention.

Reference is now made to FIG. 4 which is a schematic illustration of a small, SPECT system 100, dedicated to the nuclear imaging of the breast. Preferably, SPECT system 100 is positioned on a shaft 102 that rotates around breast 110, on an axis 104 perpendicular to the body. Rotation may be provided by a motor (not shown) or other device. In the embodiment illustrated, a patient lies prone on a table 106, facing down, and breast 110 protrudes through a hole 108 in the table, and is thus pulled down by gravity. Additionally or alternatively, the breast may be pulled out by a vacuum pump (not shown) or a radiolucent cup or other construction for extending the breast. Alternatively, the patient stands "on four" on the examination table. A chest-wall area within a diameter D is of interest. Breast 110 a height H. Optionally, a radiolucent, protective cap 116 is put on breast 110, to protect it from contact with the moving detectors.

In an embodiment of the invention, SPECT system 100 is a dual-camera SPECT system, comprising two gamma cameras 120, 180° apart, and perpendicular to the table. Preferably, each of cameras 120 is mounted on a leg 111. Optionally, a sliding mechanism 109 on shaft 102 allows the distance, W, between legs 111 to be adjusted, depending on the diameter of the breast.

In some embodiments of the invention, each camera 120 comprises a collimator 36, preferably of special design, as described below, and a detector 22. Preferably, collimator 36 and detector 22 are substantially equal in size, and have a length L, that is at least equal to breast height H. Optionally, collimator 36 has a design described below, with respect to FIGS. 5A and 5B. However, other collimator types may be used, for some aspects of the invention.

Optionally, output from each camera is sent to a computer 114, which analyzes the results and produces cross-sectional views of the breast, including the region adjacent the chest wall.

Figure 5A:
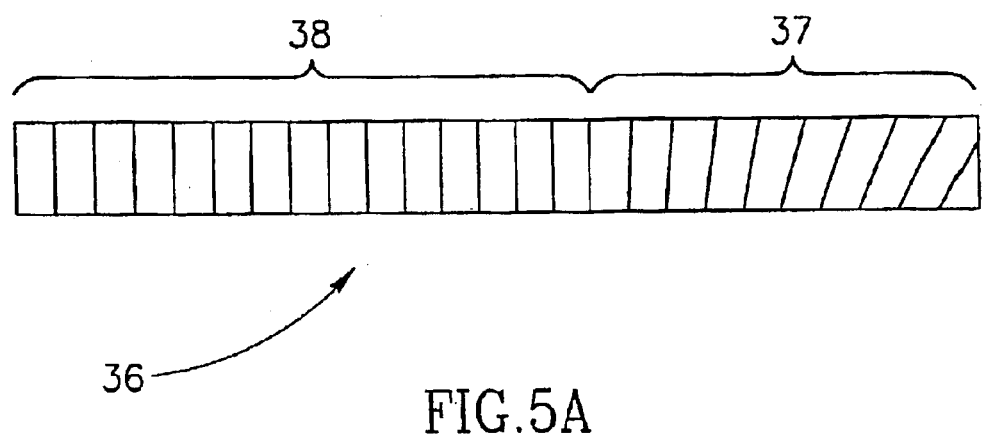
FIG. 5A is a schematic illustration of a diverging-hole collimator design for a camera-based SPECT system, dedicated to the nuclear imaging of the breast and chest wall, in accordance with an embodiment of the present invention.

Reference is now made to FIG. 5A, which is a schematic illustration of collimator 36 for nuclear imaging of the breast and chest wall, in accordance with an embodiment of the present invention. Optionally, collimator 36 comprises septa 37 whose field of view diverge near the chest wall edge of the collimator. That is to say that septa 37 view toward the chest wall rather than perpendicular to the axis of the breast. Optionally, the direction of view changes gradually away from the chest wall such that the septa 38 farther from the wall have a direction of view perpendicular to the axis and to the face of the camera. In this manner, it is possible to obtain information from the region of the breast close to the chest wall. This information cannot be obtained with a perpendicular parallel-hole collimator, with rotation around the breast. In these embodiments, reconstruction is preferably by iterative (ART) methods, as known in the art, at least for regions near the chest wall.

Figure 5B:
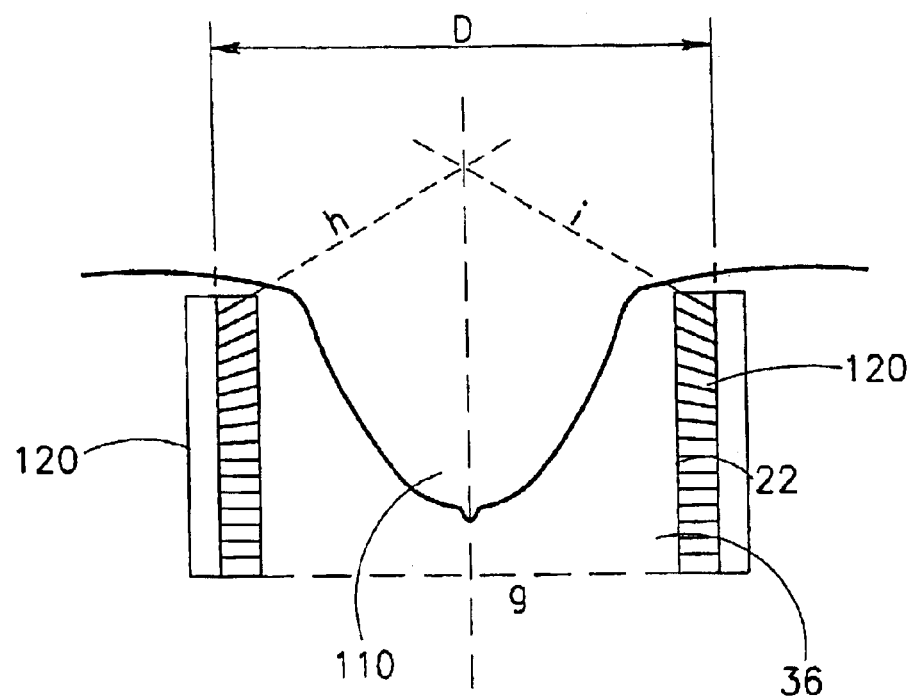
FIG. 5B is a schematic illustration of the field of view of a camera-based SPECT system with a diverging-hole collimator when imaging the breast, in accordance with an embodiment of the present invention.

Reference is now made to FIG. 5B, which is a schematic illustration of the field of view with special diverging-hole collimator 36 for a SPECT system for nuclear imaging of the breast. SPECT analysis can be obtained for the area bounded by lines g, h, and i, wherein with conventional, parallel-hole collimator, only the rectangle bounded by the two parallel cameras could have been analyzed. However, the additional information is acquired in exchanged for a certain loss in spatial resolution and an increase in artifacts, for the portion of the collimator having diverging holes. In addition, data should be acquired over 360° rotation.

Figure 6A:
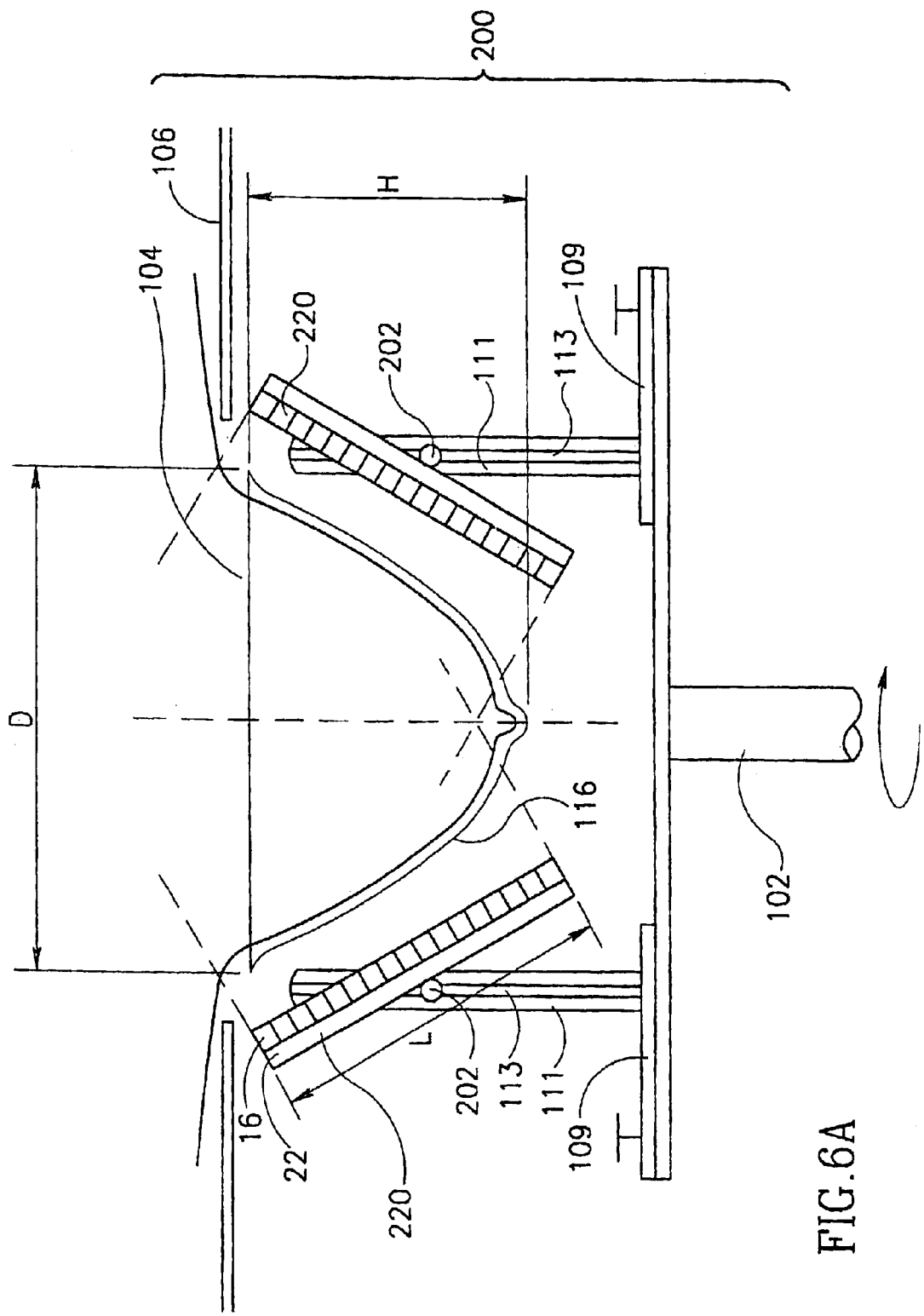
FIGS. 6A and 6B are schematic illustrations of a tiltable camera-based SPECT system dedicated to the nuclear imaging of the breast and chest wall, in accordance with embodiments of the present invention.
Figure 6B:
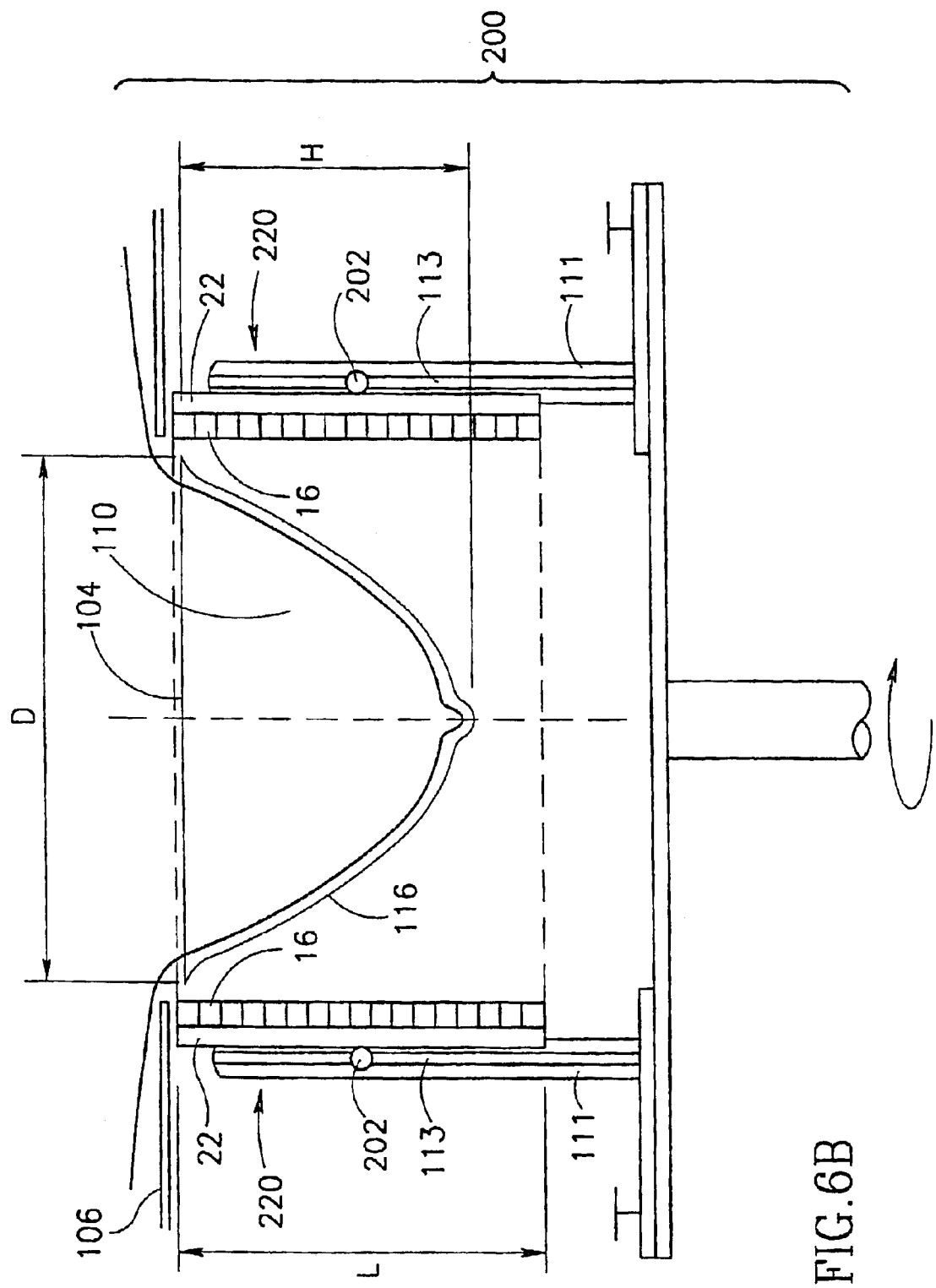

Reference is now made to FIGS. 6A and 6B which are schematic illustrations of a camera-based SPECT system, dedicated to the nuclear imaging of the breast and chest wall, wherein the camera may be tilted, in accordance with embodiments of the present invention. Optionally, camera-based SPECT system 200 comprises two cameras 220, 180° apart. Optionally, each camera 220 comprises a parallel-hole collimator 16, with septa at a right angle to the collimator length, and a detector 22.

Optionally, cameras 220 are mounted on pivots, or hinges 202, on legs 111, so that cameras 220 can be tilted so as to scan at various angles with respect to axis of the breast 104. Optionally, a sliding mechanism 109 on shaft 102 allows cameras 220 to be adjusted closer together or further apart. In some embodiments, a slot 113 on each of legs 111 allows cameras 220 to be moved up and down along axis 104.

FIG. 6A illustrates the collimator field of view when parallel-hole cameras 220 are at 30° with respect to axis 104. Data acquired using this configuration includes gamma events occurring within the breast, near the chest wall. Optionally, length L of cameras 220 is sufficiently long so that at a 30° tilt, its projection covers the complete diameter of interest, D, at the base of breast 110. However, small or larger tilt angles may be used if required to cover the breast near the wall. Preferably, as small an angle as possible is used. In this manner, chest wall information is acquired with no loss in spatial resolution. However, a second rotational pass should be made for SPECT analysis of the breast itself, as shown in FIG. 6B. Alternatively, the gamma ray activity is calculated using only the angulated camera configuration.

In some embodiments, length L of camera 220 is shorter than breast height H. When this happens, several rotational passes are made with cameras 220 parallel to breast axis 104, at different breast "heights", as mounting hinges 202 of cameras 220 are moved down slots 113 of legs 111. In exemplary embodiments of the invention, the length L of the camera is between 10 and 15 cm square and it is about 10–15 cm apart. Preferably, a size about 12 cm square is suitable.

Although the embodiments that have been described with reference to a dual-camera SPECT systems, other camera-based SPECT systems are possible. For example, the SPECT systems may comprise single scintillation camera. Alternatively, three or four scintillation cameras, arranged around the axis of rotation, may be used in order to enhance the system sensitivity.

In some embodiments of the invention, the camera-based SPECT system comprises at least one NaI(T1) crystal and an array of PMTs for position sensitivity. Alternatively, the camera-based SPECT system comprises at least one pixelated solid-state scintillation crystal, which is smaller and more suitable to the small and cramped circumstances. Alternatively, it may comprise a single position sensitive PMT.

Figure 7:
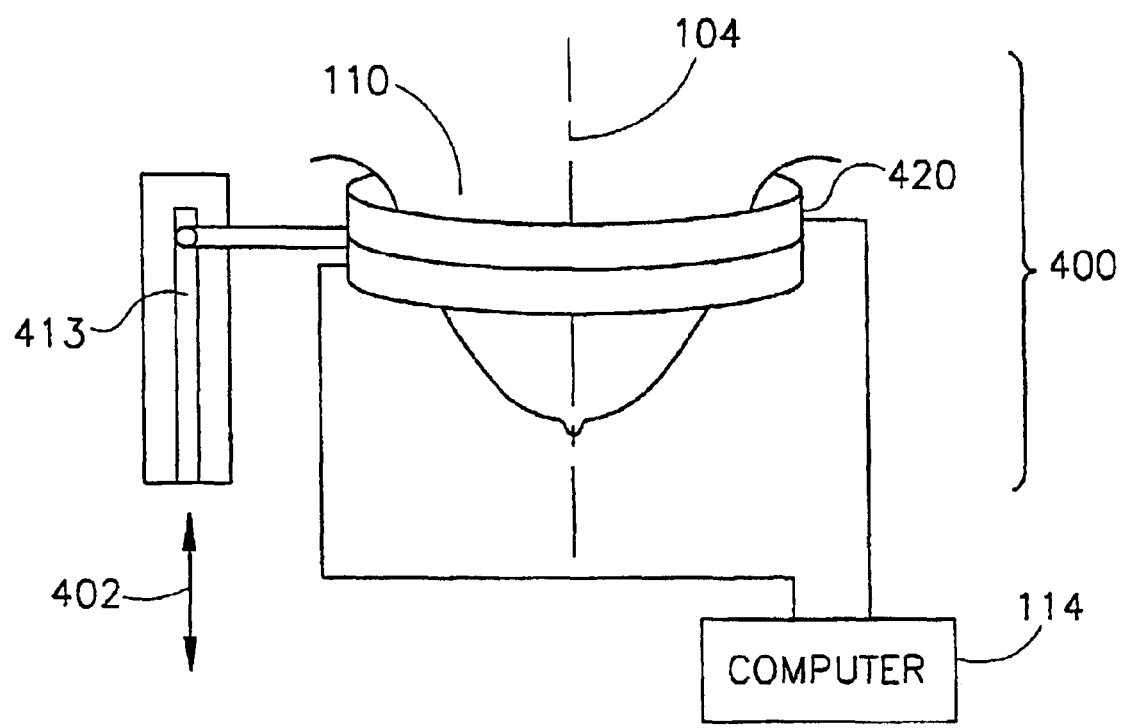
FIG. 7 is a schematic illustration of a small multidetector SPECT system dedicated to the nuclear imaging of the breast, comprising one or more stationary circular rings of detectors, in accordance with an embodiment of the present invention.

Reference is now made to FIG. 7 which is a schematic illustration of a small multidetector SPECT system 400, dedicated to the nuclear imaging of the breast, comprising one or more stationary circular rings of detectors 420, in accordance with an embodiment of the present invention. Optionally, multidetector SPECT detector system 400 has a diameter which is slightly larger than the diameter of interest at the chest wall, D. Optionally, the rings are mounted on a shaft 402 that allows travel up and down along axis 104, guided by a slot 413, and powered by a motor (not shown). Optionally, a diverging-hole collimator design is used to obtain information regarding the chest wall and the breast. Alternatively, an interchangeable collimator system is used, with a slanted, parallel-hole collimator and a right-angle, parallel-hole collimator, to obtain information regarding the chest wall and the breast. Preferably, solid state pixelated detectors, are used for the detectors in the rings. In an embodiment of the invention, the ring may be rotated by a small amount to increase resolution or may be dithered to improve image quality as described in the above referenced PCT application. Alternatively or additionally, sub-element axial motion or dithering may be provided.

Alternatively, enough rings are provided to cover the entire length of the breast. A collimator having an inward diverging view is preferably used for the rings near the chest wall.

The present invention has been described using non-limiting detailed descriptions of embodiments thereof that are provided by way of example and are not intended to limit the scope of the invention. Variations of embodiments described will occur to persons of the art. In addition, while preferred embodiments of the invention have been described as having certain groups of features, some preferred embodiments of the invention may include fewer of more of the features or other combinations of features. Furthermore, the terms "comprise," include," and "have" or their conjugates shall mean: "including but not necessarily limited to." The scope of the invention is limited only by the following claims:

What is claimed is:

1. A system, for the nuclear imaging of the breast, comprising:
    at least one gamma camera, of a size appropriate for the scanning of a breast, having a radiation detecting surface, which detects gamma radiation and provides data signals responsive to radiation from the breast;
    a collimator, positioned over the reception surface;
    a gantry on which the radiation detector is mounted and which provides rotational movement of the radiation detection surface around the axis of the breast; and
    a computer which receives and analyzes the data signals and constructs an image of radiation sources therefrom;
    wherein the radiation detection surface of the at least one gamma camera is tilted with respect to the axis during rotation of the at least one gamma camera about the axis, such that it is partially facing the chest of a study subject.

2. A system according to claim 1 and including means for selectively tilting the at least one gamma camera such that the radiation detection surface is selectively tilted or parallel to the axis of rotation, during different rotations of the at least one gamma camera about the axis.

3. A system according to claim 2, wherein the computer constructs the image of the radiation source utilizing an iterative approach for at least a portion of the volume for which data is acquired with the radiation detection surface at said angle and, wherein an analytic approach is used for at least a part of the volume for which data is acquired with the radiation detection surface parallel to the axis of rotation.

4. A system according to claim 1 wherein the computer constructs the image of radiation sources utilizing an iterative approach for at least part of a reconstructed volume.

5. A system according to claim 1 wherein the detector is a detector having an extent between 10 and 20 cm.

6. A system according claim 5 wherein the extent is between 10 and 15 cm.

7. A system according to claim 5 wherein the extent is about 12 cm.

8. A system according to claim 1 wherein the at least one planar gamma camera comprises two detection surfaces, each said surface being tilted with respect to the axis during rotation of the at least one gamma camera about the axis, such that it ii partially facing the chest of a study subject.

9. A system according to claim 1 wherein the image is a SPECT image.

10. A system, for the nuclear imaging of the breast, comprising:
- at least one gamma camera, of a size appropriate for the scanning of a breast, having a radiation detecting surface, which detects gamma radiation and provides data signals responsive to radiation from the breast;
- a collimator, positioned over the reception surface;
- a gantry on which the radiation detector is mounted and which provides rotational movement of the radiation detection surface around the axis of the breast; and
- a computer which receives and analyzes the data signals and constructs an image of radiation sources therefrom;
- wherein the collimator comprises sepia near the center of the collimator which accept radiation from a direction perpendicular to the radiation detection surface and septa near an edge of the collimator which accept radiation from an outward facing acute angle to the perpendicular direction.

11. A system according to claim 10 wherein the septa which accept radiation near one edge accept such radiation only near one edge of the collimator.

12. A system according to claim 11 wherein the one edge is an edge near the chest wall of the study subject.

13. A system according to claim 10 wherein the computer constructs the image of radiation sources utilizing an iterative approach for at least part of a reconstructed volume.

14. A system according to claim 10 wherein the computer constructs the image of the radiation source utilizing an iterative approach for at least a portion of the volume for which data is acquired via the septa at said angle and wherein an analytic approach is used for at least a part of the volume for which data is acquired via the septa normal to the direction of the axis.

15. A system according to claim 10 wherein the image is a SPECT image.

16. A gamma ray detector system comprising:
- at least one gamma ray detector having a detector surface that has a normal thereto at each point thereof; and
- at least one collimator placed on the detector surface, the collimator having a first portion that selectively passes gamma rays which impinge it at said normal angle and at angles near said angle and a second portion that selectively passes gamma rays which impinge on it from an outward looking direction with respect to the normal;
- wherein the first portion comprises a region near one edge of the collimator and a central region of the collimator and wherein the second portion comprises a region near a second edge of the collimator opposite the one edge.

17. A gamma ray detector system according to claim 16 wherein the at least one detector surface is a planar surface and wherein the first portion comprises the entire planar surface except for a region near the second edge.

18. A gamma ray detector system according to claim 17 wherein the planar surface has an extent of less than 20 cm.

19. A gamma ray detector system according to claim 17 wherein the planar surface has an extent of less than about 15 cm.

20. A gamma ray detector system according to claim 17 wherein the at least one detector comprises first and second detectors said first detector and second detectors having first and second detector surfaces that are parallel and face each other, each said detector having a collimator placed thereon, as aforesaid.

21. A gamma ray detector system according to claim 20 wherein the second portions of the collimators associated with the first and second detectors are situated opposite each other.

22. A gamma ray detector system according to claim 16 wherein the detector surface comprises a cylindrical surface and wherein the first portion comprises the detector surface except for a region near one end of the cylindrical surface.

23. A gamma ray detector system according to claim 22 wherein the cylindrical surface has an inner diameter of between 10 and 20 cm.

24. A gamma ray detector system according to claim 23 wherein the collimator has an inner diameter of less than 20 cm.

25. A gamma ray detector system according to claim 23 wherein the collimator has an inner diameter of less than about 15 cm.

26. A gamma camera comprising:
- a gamma ray detector system according to claim 22 and including a rotator that rotates the at least one detector surface about an axis parallel to and within the field of view of the detector surface, wherein the outward looking direction is at an acute angle with the axis.

27. A gamma camera according to claim 26 wherein the outward looking angle varies over the second portion, with said angle being 90 degrees near the first portion and a minimum value near at the second edge.

28. A gamma camera according to claim 27 wherein the minimum value is about 60 degrees.

29. A gamma camera according to claim 27 wherein the minimum value is about 60 degrees.

30. A gamma camera according to claim 26 wherein the gamma ray detector system is sized and configured to rotate about a breast of a human patient, wherein the axis of rotation coincides generally with the axis of the breast.

31. A gamma camera according to claim 26 wherein the at least one detector generates nuclear medicine imaging signals responsive to gamma rays detected by the at least one detector and including image processing circuitry that receives said signals and produces a three dimensional image therefrom.

32. A gamma camera according to claim 31 wherein the image processing circuitry produces said image utilizing an Iterative approach for a portion of the image, said portion including at least the portion including information acquired from the outward looking direction.

33. A gamma camera according to claim 22 wherein the outward looking angle varies over the second portion, with said angle being 90 degrees near the first portion and having a minimum value near at the second edge.

34. A gamma camera according to claim 22 wherein the gamma ray detector system is sized and configured to fit around the breast of a human patient, wherein the axis of the cylinder coincides generally with the axis of the breast.

35. A gamma camera according to claim 22 wherein the cylindrical detector generates nuclear medicine imaging signals responsive to gamma rays detected by the detector and including image processing circuitry that receives said signals and produces a three dimensional image therefrom.

36. A system, for the nuclear imaging of an object comprising:
- at least one planar gamma camera, having a planar radiation detecting surface, which detects gamma radiation and provides data signals responsive to radiation from the object;
- a collimator, positioned over the reception surface;
- a gantry on which the radiation detector is mounted and which provides rotational movement of the radiation detection surface around an axis, such that the radiation detector detects radiation from different direction as it rotates around the axis; and a computer which receives and analyzes the data signals and constructs tomographic image of radiation sources therefrom;

wherein the radiation detection surface of the at least one gamma camera is tilted with respect to the axis during rotation of the at least one gamma camera about the axis, such that a normal to the detection surface forms an acute angle with axis.

37. A system according to claim 36 wherein the at least one planar gamma camera comprises two detection surfaces, each said surface being tilted with respect to the axis during rotation of the at least one gamma camera about the axis, such that a normal to the detection surface forms an acute angle with axis.

* * * * *